United States Patent [19]
Tanaka et al.

[11] Patent Number: 5,312,815
[45] Date of Patent: May 17, 1994

[54] FUNGICIDAL (+)-2-(2,4-DIFLUOROPHENYL)-3-METHYL-1-(1H-1,2,4-TRIAZOL-1-YL)3-(6-(1H-1,2,4-TRIAZOL-1-YL)PYRIDAZIN-3-YLTHIO)BUTAN-2-OL

[75] Inventors: Yuji Tanaka; Teruyuki Yuasa; Yoshinari Kawakami; Kohji Terashima, all of Shiga; Tatsuya Morita, Hokkaido; Atsushi Nishikawa; Masaji Kawashima, both of Shiga, all of Japan

[73] Assignee: Roussel Morishita Co., Ltd., Osaka, Japan

[21] Appl. No.: 8,750

[22] Filed: Jan. 25, 1993

[30] Foreign Application Priority Data

Jan. 24, 1992 [JP] Japan .................. 4-034132

[51] Int. Cl.⁵ .............................. A61K 31/50
[52] U.S. Cl. ...................... 514/58; 514/252; 544/238; 536/46
[58] Field of Search ............ 514/58, 252; 544/238

[56] References Cited

U.S. PATENT DOCUMENTS

| | | | |
|---|---|---|---|
| 4,011,218 | 3/1977 | Baldwin et al. | 544/238 |
| 4,256,887 | 3/1981 | Novello et al. | 544/238 |
| 4,764,604 | 8/1988 | Müller | 544/238 |
| 4,883,785 | 11/1989 | Chow et al. | 514/58 |
| 5,177,094 | 1/1993 | Itoh et al. | 514/383 |

FOREIGN PATENT DOCUMENTS

| | | |
|---|---|---|
| 0200118 | 11/1986 | European Pat. Off. |
| 0395985 | 11/1990 | European Pat. Off. |
| 0421210A2 | 4/1991 | European Pat. Off. |
| 0421210 | 4/1991 | European Pat. Off. |
| 0446877 | 9/1991 | European Pat. Off. |
| 58-189173 | 11/1983 | Japan |

*Primary Examiner*—Donald G. Daus
*Attorney, Agent, or Firm*—Sughrue, Mion, Zinn, Macpeak & Seas

[57] ABSTRACT

(+)-2-(2,4-Difluorophenyl)-3-methyl-1-(1H-1,2,4-triazol-1-yl)-3-(6-(1H-1,2,4-triazol-1-yl)pyridazin-3-ylthio)butan-2-ol and a pharmaceutically acceptable salt thereof useful as an antifungal agent are disclosed. An inclusion complex of the compound with cyclodextrin can be given either orally or intravenously and has increased absorption when administered orally.

10 Claims, 1 Drawing Sheet

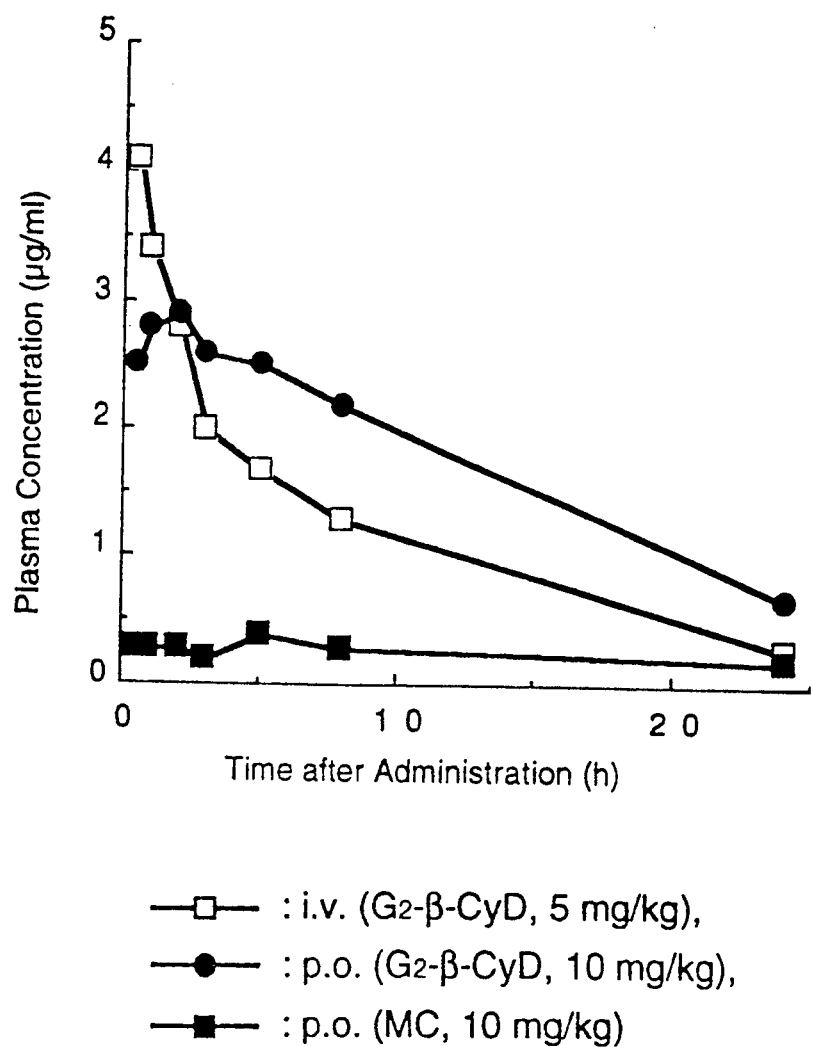
FIGURE I
—□— : i.v. (G2-β-CyD, 5 mg/kg),
—●— : p.o. (G2-β-CyD, 10 mg/kg),
—■— : p.o. (MC, 10 mg/kg)

FUNGICIDAL (+)-2-(2,4-DIFLUOROPHENYL)-3-METHYL-1-(1H-1,2,4-TRIAZOL-1-YL)3-(6-(1H-1,2,4-TRIAZOL-1-YL)PYRIDAZIN-3-YLTHIO) BUTAN-2-OL

FIELD OF THE INVENTION

The present invention relates to a 1-aryl-2-(1H-1,2,4-triazol-1-yl)ethanol derivative useful as an anti-fungal agent and to antifungal compositions containing that derivative.

BACKGROUND OF THE INVENTION

In recent years, deep mycoses caused by opportunistic fungal infection have been increasing with the frequent use of steroids, carcinostatic agents, and immunosuppressants as well as with the prevalence of acquired immunodeficiency syndrome (AIDS).

Conventional antifungals involve various clinical problems and are not necessarily deemed to be satisfactory drugs. For example, amphotericin B, though exhibiting extremely potent antifungal activities, also has serious side effects, such as hyperthermia and renal insufficiency, which have limited usefulness of the drug. 5-Fluorocytosine is apt to develop resistant fungi. Ketoconazole induces hepatotoxicity following maintained administration of large doses and, in addition, oral preparations but not intravenous injections are available. On the other hand, fluconazole has been frequently used clinically because of its relatively low toxicity and availability in both oral preparations and intravenous injections. However, it has a low inhibitory activity against aspergillosis, and the development of resistance has recently given rise to a problem. Further, itraconazole, of the same triazole type, is only available in oral preparations and cannot be administered to those patients who cannot receive a treatment by mouth. It is also deemed unsatisfactory in terms of potency and pharmacokinetics.

Deep mycoses are, for the most part, candidosis, cryptococcosis, and aspergillosis, and how to treat these infectious diseases, especially aspergillosis has been a clinically important subject.

EP 0421210A2 and JP-A-58-189173 (the term "JP-A" as herein means an "unexamined published Japanese patent application" disclose 1-aryl-2-(1H-1,2,4-triazol-1-yl)-ethanol derivatives but gives no mention of the specific compound of the present invention.

SUMMARY OF THE INVENTION

An object of the present invention is to provide an antifungal composition which is low in toxicity, which exerts an excellent inhibitory activity against not only aspergillosis but other deep mycoses, and which can be given either orally or intravenously.

The inventors have conducted extensive and intensive investigations and, as a result, found that the compound represented by formula (I) shown below and its pharmaceutically acceptable salt are not only strikingly effective against aspergillosis but also against other deep mycoses. They have further found that an inclusion complex of the compound of formula (I) and cyclodextrin may be formulated as an intravenously injectable solution and that oral administration of this inclusion complex has an increased absorption and maintains a higher level in the blood.

The present invention relates to (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol (dextrorotatory enantiomer) represented by formula (I):

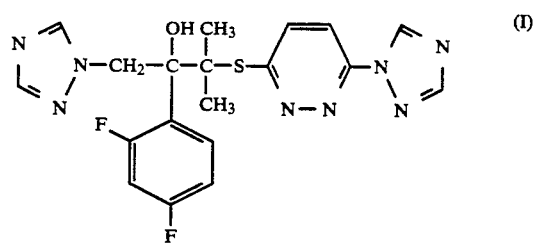

or a pharmaceutically acceptable salt thereof.

The present invention also relates to an anti-fungal composition containing the compound of formula (I) or a pharmaceutically acceptable salt thereof as an active ingredient.

The present invention further relates to an antifungal composition mainly comprising an inclusion complex composed of the compound of formula (I) or a pharmaceutically acceptable salt thereof and cyclodextrin.

BRIEF DESCRIPTION OF THE DRAWINGS

FIG. 1 is a graph showing changes in plasma level with the compound of the present invention over time after oral administration and with the compound of the present invention in an inclusion complex thereof with maltosyl-$\beta$-cyclodextrin ($G_2$-$\beta$-CyD) after oral administration and intravenous administration.

DETAILED DESCRIPTION OF THE INVENTION

The pharmaceutically acceptable salts of the compound of formula (I) include: inorganic acid salts, such as a hydrochloride, a hydrobromide, a sulfate and a phosphate; and organic acid salts, such as an acetate, a lactate, a fumarate, a maleate, a malate, a tartrate, a citrate, an aspartate and a methanesulfonate.

An inclusion complex of the compound of formula (I) or a pharmaceutically acceptable salt thereof with cyclodextrin can be prepared according to the following manner. The compound of formula (I) or a pharmaceutically acceptable salt thereof and cyclodextrin are dissolved in water by mixing and heating them. The solution is then lyophilized or its solvent is removed under reduced pressure to obtain an inclusion complex of the compound of formula (I) or a pharmaceutically acceptable salt thereof with cyclodextrin.

Cyclodextrin to be used in the preparation of the inclusion complex according to the present invention includes $\alpha$-, $\beta$- or $\gamma$-cyclodextrin or derivatives thereof, such as a hydroxypropyl derivative, a hydroxyethyl derivative, a glucosyl derivative and a maltosyl derivative. The cyclodextrin is usually used in an amount of from 1 to 15 mols per mol of the compound of formula (I) or a salt thereof.

The compound of formula (I) of the present invention can be prepared by, for example, reacting a compound represented by formula (II):

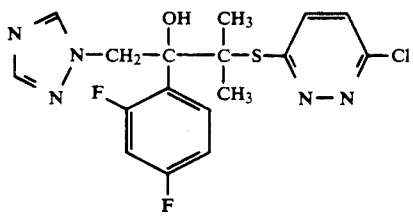
(II)

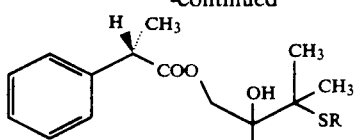
(IV)

with 1,2,4-triazole in an appropriate solvent, such as a nitrile (e.g., acetonitrile). The reaction is usually carried out at a temperature of from room temperature to 150° C., and preferably from 50° to 110° C. While varying depending on the kind of solvent used and the reaction temperature, the reaction time usually ranges from 1 to 150 hours. 1,2,4-Triazole is usually used in an amount of at least 1 mol, and preferably from 1 to 5 mols, per mol of the compound (II).

The starting compound (II) can be prepared according to the following reaction scheme. EP 0421210A2 supra discloses the intermediate compound (XIII) shown in the scheme as a racemate without specifically describing the process for preparation and physical properties of that compound.

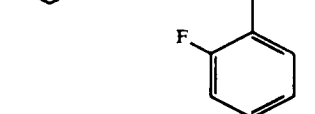
(X)

(XI)

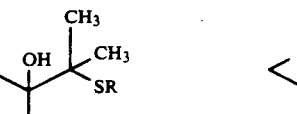
(XII)

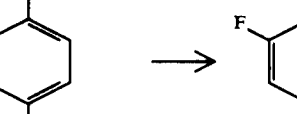
(XIII)

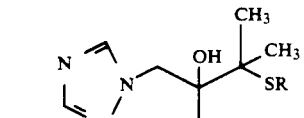

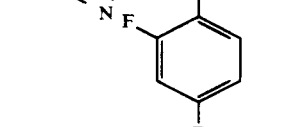
(II)

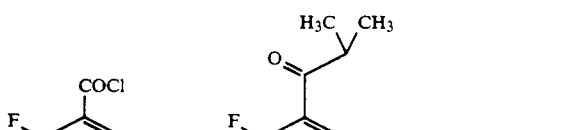
(III)    (IV)

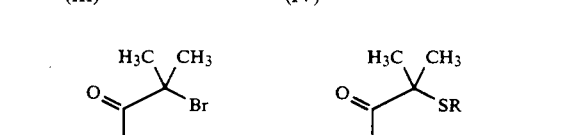
(V)    (VI)

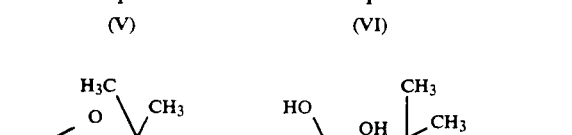
(VII)    (VIII)

wherein R represents a 4-methoxybenzyl group.

Compound (III) is reacted with isopropylmagnesium bromide in a solvent in the presence of a transition metal catalyst to obtain comound (IV). Examples of suitable solvents include ethers, e.g., diethyl ether, tetrahydrofuran (THF), 1,4-dioxane, and 1,2-dimethoxyethane. Examples of suitable transition metal catalysts include copper (I) chloride, copper (II) chloride, copper (I)

bromide, copper (II) bromide, copper (I) iodide, ferric (III) chloride, cobalt (II) bromide, nickel (II) chloride, palladium (II) chloride, manganese (II) chloride, and silver (I) bromide. The reaction is usually carried out at a temperature of from −78° C. to room temperature, and preferably of from −40° to 0° C., for a period of from 1 to 24 hours. Isopropylmagnesium bromide is usually used in an amount of at least 1 mol, and preferably 1 to 2 mols, per mol of compound (III). The transition metal catalyst is usually used in an amount of from 0.01 to 1.0 mol, and preferably from 0.03 to 0.1 mol, per mol of compound (III).

Compound (IV) is reacted with bromine in a solvent to obtain compound (V). Examples of suitable solvents include: halogenated hydrocarbons, e.g., methylene chloride and chloroform; organic acids, e.g., acetic acid; and ethers, e.g., diethyl ether, THF, 1,4-dioxane, and 1,2-dimethoxyethane. The reaction is usually carried out at a temperature of from −20° to 50° C., and preferably from −10° C. to room temperature, for a period of from 1 to 10 hours. Bromine is used in an amount of at least 1 mole, and preferably from 1.0 to 1.5 mols, per mol of compound (IV).

Compound (V) is reacted with 4-methoxy-α-toluenethiol in a solvent in the presence of a base to obtain compound (VI). Examples of suitable solvents include: ethers, e.g., THF, diethyl ether, 1,4-dioxane, and 1,2-dimethoxyethane; and amides, e.g., N,N-dimethylformamide (DMF) and N,N-dimethylacetamide (DMA). Examples of suitable bases include: sodium methoxide, sodium ethoxide, sodium carbonate, potassium carbonate, and sodium hydride. The reaction is usually carried out at a temperature of from −78° to 50° C., and preferably from −10° C. to room temperature, for a period of from 1 to 24 hours. 4-Methoxy-α-toluenethiol and the base are both used in an amount of at least 1 mol, and preferably 1.0 to 1.2 mols, per mol of compound (V).

Compound (VI) is reacted with dimethyloxosulfonium methylide in a known manner to obtain compound (VII) (see, e.g., *J. Amer. Chem. Soc.*, Vol. 87, p. 1353 (1965)).

Compound (VII) is reacted with not less than 1 equivalent of an alkali metal acetate in a solvent in the presence of a phase transfer catalyst to obtain compound (VIII). Suitable solvents include a mixed solvent of water and an amide, e.g., DMA or DMF, or a nitrile, e.g., acetonitrile. The alkali metal acetate includes potassium acetate, sodium acetate, and lithium acetate. The phase transfer catalyst includes cyclic polyethers, e.g., 18-crown-6 and 15-crown-5, and amines, e.g., N,N,N',N'-tetramethylethylenediamine. The phase transfer catalyst is usually used in an amount of from 0.05 to 3 mols, and preferably from 0.1 to 1.5 mols, per mol of compound (VII). The reaction is usually carried out at a temperature from 60° to 200° C., and preferably from 90° to 150° C., for 1 to 72 hours.

Compound (VIII) is reacted with not less than 1 equivalent of an optically active carboxylic acid in a solvent in the presence of an additive, e.g., 4-dimethylaminopyridine, and a dehydrating agent, e.g., 1,3-dicyclohexylcarbodiimide, to obtain compound (IX). Suitable solvents include halogenated hydrocarbons, e.g., methylene chloride and chloroform, and ethers, e.g., THF and 1,4-dioxane. While not limited thereto, the optically active carboxylic acid suitably includes (S)-(+)-2-phenylpropionic acid. The reaction is usually carried out at −78° C. to room temperature for 0.1 to 12 hours. The resulting compound (IX) is a mixture of diastereomers and can be easily separated by column chromatography on silica gel.

Compound (IX) is then subjected to hydrolysis to obtain compound (X).

Compound (X) is reacted with methanesulfonyl chloride in pyridine, followed by alkali treatment in a known manner, to obtain compound (XI).

Compound (XI) is reacted with 1,2,4-triazole in a solvent in the presence of a base to obtain compound (XII). Examples of suitable solvents include nitriles, e.g., acetonitrile, and amides, e.g., DMF and DMA. Examples of suitable bases include sodium carbonate, potassium carbonate, and sodium hydride. The reaction is usually carried out at room temperature to 170° C., and preferably 60° to 120° C., for 1 to 24 hours. 1,2,4-Triazole and the base are both used in an amount usually of at least 1 mol, and preferably from 1.0 to 3 mols, per mol of compound (XI).

Compound (XII) is reacted with trifluoroacetic acid in the presence of at least one equivalent of anisole usually at −20° to 80° C., and preferably from room temperature to 70° C., for 0.1 to 3 hours to obtain compound (XIII).

Compound (XIII) is reacted with 3,6-dichloropyridazine in a solvent in the presence of a base to obtain Compound (II). Example of suitable solvents include: ether, e.g., THF, diethyl ether, 1,4-dioxane, and 1,2-dimethoxyethane; and amides, e.g., DMF and DMA.

Examples of suitable bases include: sodium methoxide, sodium ethoxide, sodium carbonate, potassium carbonate, and sodium hydride. The reaction is usually carried out at −20° to 50° C., and preferably −10° C. to room temperature, for 0.1 to 24 hours. 3,6-Dichloropyridazine and the base are both used in an amount of at least 1 mol, and preferably 1.0 to 5 mols, per mol of compound (XIII).

The compound according to the present invention can be formulated, together with pharmaceutically acceptable adjuvants, such as vehicles, carriers, diluents, etc., into various dose forms for oral or non-oral administration, such as tablets, capsules, granules, particles, powders, pills, syrups, suspensions, emulsions, ointments, suppositories, and injectable solutions.

The dose of the compound may be selected appropriately depending on the symptoms, the age or body weight of the patient, and the like. For example, a recommended oral dose for adults is from 50 to 1000 mg per day, usually given in a single does or several divided doses.

The present invention is now illustrated in greater detail with reference to Examples, Reference Examples, Formulation Examples, and Test Examples, but it should be understood that the present invention is not limited thereto. All the percentages are by weight unless otherwise indicated. All the ratios of mixed solvents used for column chromatography are by volume.

EXAMPLE 1

A mixture consisting of 3.0 g (7.3 mmol) of (+)-3-(6-chloropyridazin-3-ylthio)-2-(2,4-difluorophenyl)-3-methyl-1-(1H-1,2,4-triazol-1-yl)butan-2-ol 2.0 g(29 mmol) of 1,2,4-triazole, and 1.5 ml of acetonitrile was heated at reflux for 19 hours. After allowing the mixture to cool, the solvent was removed by distillation under reduced pressure, and the residue was neutralized with a saturated aqueous solution of sodium hydrogencarbonate, followed by extraction with chloroform. The organic layer was washed successively with water and a saturated sodium chloride aqueous solution and dried. The solvent was distilled off under reduced pressure, and the residue was subjected to column chromatography using a mixed solvent of chloroform and methanol (100:1). The solvent was removed from the effluent by distillation under reduced pressure, and the residue was recrystallized from a mixed solvent of chloroform and diethyl ether to obtain 3.0 g (93%) of (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol as a colorless crystal.

Melting Point: 226–227° C.
$[\alpha]^{25} +134.4°$ (c=1.05, $CHCl_3$)
IR (nujol) $\nu_{max}$ cm$^{-1}$: 1608, 1510
NMR ($CDCl_3$): 1.59 (3H, s), 1.65 (3H, d, J=2.7Hz), 4.90
(1H, d, J=13.6Hz), 5.42 (1H, d, J=13.7Hz), 6.67–6.85 (2H, m), 7.65–7.95 (4H, m), 8.08 (1H, d, J=9.2Hz), 8.19 (1H, s), 8.30 (1H, s), 9.36 (1H, s)

EXAMPLE 2

A mixture consisting of 1.6 g (3.9 mmol) of (+)-3-(6-chloropyridazin-3-ylthio)-2-(2,4-difluorophenyl)-3-methyl-1-(1H-1,2,4-triazol-1-yl)butan-2-ol, 1.0 g (14.5 mmol) of 1,2,4-triazole, 1.0 g (7.2 mmol) of potassium carbonate, 2.2 g (14.7 mmol) of sodium iodide, and 20 ml of acetonitrile was heated at reflux for 116 hours. After allowing the mixture to cool, the solvent was removed by distillation under reduced pressure, and to the residue was added a saturated sodium chloride aqueous solution, followed by extraction with dichloromethane. The organic layer was washed successively with 10% sodium thiosulfate aqueous solution and a saturated sodium chloride aqueous solution and dried. The solvent was removed by distillation under reduced pressure, and the residue was subjected to column chromatography using a mixed solvent of chloroform and methanol (100:1). The solvent was removed by distillation under reduced pressure, and the residue was recrystallized from a mixed solvent of isopropyl ether and methanol to obtain 1.2 g (70%) of (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol as a colorless crystal.

Melting Point: 226–227° C.
$[\alpha]^{25\ 30}\ 121.0°$ (c=1.05, $CHCl_3$)
IR (nujol) $_{84\ max}$ cm$^{-1}$: The data were identical with those obtained in Example 1.
NMR ($CDCl_3$) The data were identical with those obtained in Example 1.

REFERENCE EXAMPLE 1

To a mixture of 120 g (0.68 mmol) of 2,4-difluorobenzoyl chloride, 3.7 g (37 mmol) of copper (I) chloride, and 400 ml of diethyl ether was added dropwise 442 ml of diethyl ether containing 130.2 g (0.88 mol) of isopropylmagnesium bromide at −25° C. over 4 hours. The temperature was elevated up to −5° C., and the mixture was stirred at that temperature for 30 minutes. To the reaction mixture were added dropwise 150 ml of water and then 120 ml of 6N hydrochloric acid. The organic layer was separated, washed successively with 5% hydrochloric acid, a saturated sodium chloride aqueous solution, a saturated sodium carbonate aqueous solution, and a saturated sodium chloride aqueous solution, and dried. The solvent was removed by distillation under reduced pressure, and the residue was distilled under reduced pressure to obtain 104.3 g (83%) of 1-(2,4-difluorophenyl)-2-methylpropan-1-one as a colorless oily substance.

Boiling Point: 56° C./2 mmHg
IR (film) $\nu_{max}$ cm$^{-1}$: 1694
NMR ($CDCl_3$): 1.18 (3H, s), 1.21 (3H, s), 3.28–3.47 (1H, m), 6.81–7.00 (2H, m), 7.81–7.91 (1H, m)

REFERENCE EXAMPLE 2

In 260 ml of methylene chloride was dissolved 145.5 g (0.79 mol) of 1-(2,4-difluorophenyl)-2-methylpropan-1-one, and 134.2 g (0.84 mol) of bromine was slowly added dropwise thereto at 20° C. or lower. The mixture was warmed to room temperature and stirred for 1 hour. A saturated sodium chloride aqueous solution and a saturated sodium thiosulfate aqueous solution were added to the reaction mixture. The organic layer was separated, washed successively with a saturated sodium chloride aqueous solution, a saturated sodium hydrogencarbonate aqueous solution, and a saturated sodium chloride aqueous solution, and dried. The solvent was removed by distillation under reduced pressure to obtain 205.7 g (99%) of 2-bromo-1-(2,4-difluorophenyl)-2-methylpropan-1-one as a pale yellow oily substance.

IR (film) $\nu_{max}$ cm$^{-1}$: 1708
NMR ($CDCl_3$): 1.97 (6H, s), 6.81–7.00 (2H, m), 7.67–7.77 (1H, m)

REFERENCE EXAMPLE 3

In 180 ml of THF was suspended 2.4 g (60 mmol) of 60% sodium hydride having been washed with hexane, and 9.4 g (61 mmol) of 4-methoxy-α-toluenethiol was added dropwise to the suspension while stirring under ice-cooling. After being stirred for 10 minutes, the mixture was added dropwise to a solution of 15.0 g (57 mmol) of 2-bromo-1-(2,4-difluorophenyl)-2-methylpropan-1-one in 225 ml of THF with stirring under ice-cooling. To the reaction mixture were added diethyl ether and water, and the organic layer was separated, washed with water and then with a saturated sodium chloride aqueous solution, and dried. The solvent was removed by distillation under reduced pressure, and the residue was subjected to column chromatography using a mixed solvent of hexane and ethyl acetate (10:1). The solvent was removed by distillation under reduced pressure to obtain 19.2 g (95%) of 1-(2,4-difluorophenyl)-2-((4-methoxyphenyl)methylthio)-2-methylpropan-1-one as a colorless oily substance.

IR (film) $\nu_{max}$ cm$^{-1}$: 1686
NMR ($CDCl_3$): 1.52 (6H, s), 3.66 (2H, s), 3.79 (3H, s), 6.81–6.91 (2H, m), 6.84 (2H, d, J=8.8Hz), 7.21 (2H, d, J=8.7Hz), 7.61–7.71 (1H, m)

REFERENCE EXAMPLE 4

In 900 ml of dimethyl sulfoxide was suspended 41.2 g (1.0 mol) of 60% sodium hydride having been washed with hexane, and 226.7 g (1.0 mol) of trimethyloxosulfonium iodide was added to the suspension in divided portions with stirring under cooling with ice. After the evolution of hydrogen gas ceased, stirring was continued at room temperature for an additional 2-hour period. A solution of 193.0 g (0.57 mmol) of 1-(2,4-difluorophenyl)-2-((4-methoxyphenyl)methylthio)-2-methylpropan-1-one in 110 ml of dimethyl sulfoxide was added thereto, followed by stirring for 12 hours. The reaction mixture was poured into ice-water, followed by extraction with ethyl acetate. The organic layer was washed with a saturated sodium chloride aqueous solution and dried. The solvent was removed by distillation under reduced pressure. The residue was subjected to column chromatography and eluted with a mixed solvent of hexane and ethyl acetate (10:1). The solvent was removed by distillation under reduced pressure, and the residue was recrystallized from a mixed solvent of diethyl ether and hexane to obtain 135.8 g (68%) of (±)-2-(2,4-difluorophenyl)-2-(1-((4-methoxyphenyl)methylthio)-1-methylethyl)oxirane as a colorless crystal.

Melting Point: 65–66° C.
IR (nujol) $v_{max}$ cm$^{-1}$: 972
NMR (CDCl$_3$): 1.37 (3H, s), 1.38 (3H, s), 2.78 (1H, d, J=4.9Hz), 3.38 (1H, d, J=4.9Hz), 3.79 (3H, s), 3.88 (2H, s), 6.74–6.93 (2H, m), 6.84 (2H, d, J=8.7Hz), 7.25 (2H, d, J=8.7Hz), 7.49–7.59 (1H, m)

REFERENCE EXAMPLE 5

A solution of 1.12 g (11.4 mmol) of potassium acetate in 2 ml of water was added to a solution of 2.0 g (5.7 mmol) of (±)-2-(2,4-difluorophenyl)-2-(1-((4-methoxyphenyl)methylthio)-1-methylethyl)oxirane and 0.15 g (0.57 mmol) of 18-crown-6 in 12 ml of DMA, and the mixture was stirred at 110° C. for 30 hours. After being allowed to cool, 50 ml of water was added to the reaction mixture, followed by extraction with ethyl acetate. The organic layer was washed with a saturated sodium chloride aqueous solution, dried, and distilled under reduced pressure to remove the solvent. The residue was purified by column chromatography using a mixed solvent of hexane and ethyl acetate (5:1) as an eluent. The solvent was removed by distillation under reduced pressure, and the residue was recrystallized from a mixed solvent of isopropyl ether and diethyl ether to obtain 1.58 g (75%) of (±)-2-(2,4-difluorophenyl)-3-((4-methoxyphenyl)methylthio)-3-methylbutane-1,2-diol as a colorless crystal.

Melting Point: 113° C.
IR (nujol) $v_{max}$ cm$^{31\ 1}$: 3324
NMR (CDCl$_3$) 1.32 (3H, s), 1.34 (3H, s), 2.50–2.60 (1H, m), 3.78 (1H, s), 3.79 (3H, s), 3.83 (2H, s), 4.15–4.27 (1H, m), 4.27–4.44 [1H, m], 6.70–6.96 (2H, m), 6.84 (2H, d, J=8.7Hz), 7.22 (2H, d, J=8.7Hz), 7.69–7.80 (1H, m)

REFERENCE EXAMPLE 6

A solution of 11.7 g (56.7 mmol) of 1,3-dicyclohexylcarbodiimide in 38 ml of dichloromethane was added dropwise to a mixture of 14.0 g (38.0 mmol) of (±)-2-(2,4-difluorophenyl)-3-((4-methoxyphenyl)methylthio)-3-methylbutane-1,2-diol, 6.3 g (41.8 mmol of (S)-(+)-2-phenylpropionic acid, 0.47 g (3.8 mmol) of 4-dimethylaminopyridine, and 190 ml of dichloromethane with stirring under ice-cooling, followed by stirring for 3 hours. The mixture was warmed to room temperature, and the stirring was continued for 12 hours. Ethyl acetate was added to the reaction mixture, and the precipitated insoluble matter was removed by filtration. The filtrate was washed successively with a saturated sodium hydrogencarbonate aqueous solution and a saturated sodium chloride aqueous solution, and dried. The solvent was removed by distillation under reduced pressure, and the residue was purified by column chromatography using a mixed solvent of hexane and ethyl acetate (10:1) as an eluent. The solvent was removed from each fraction by distillation under reduced pressure to obtain diastereomers (A-1) and (A-2) of 2-(2,4-difluoro-phenyl)-2-hydroxy-3-((4-methoxyphenyl)methylthio)-3-methylbutyl (S)-(+)-2-phenylpropionate in a yield of 9.3 g (49%) and 8.7 g (46%), respectively, as a colorless oily substance.

(A-1)
$[\alpha]^{25}$+15.9° (c=1.09, MeOH)
IR (film) $v_{max}$ cm$^{-1}$: 3444, 1742, 1716
NMR (CDCl$_3$): 1.28 (3H, s), 1.30 (3H, s), 1.33 (3H, d, J=7.2Hz), 1.50–1.75 (1H, bs), 3.57 (1H, q, J=7.2Hz), 3.75–3.88 (2H, m), 3.78 (3H, s), 4.88–4.91 (2H, m), 6.50–6.60 (1H, m), 6.76–6.87 (1H, m), 6.82 (2H, d, J=8.7Hz), 6.90–7.05 (2H, m), 7.05–7.25 (3H, m), 7.21 (2H, d, J=8.7Hz), 7.53–7.64 (1H, m)

(A-2)
$[\alpha]^{25}$+13 3° (c=1.03, MeOH)
IR (film) $v_{max}$ cm$^{-1}$: 3484, 1740
NMR (CDCl$_3$): 1.29 (3H, s), 1.33 (3H, s), 1.33 (3H, d, J=7.1Hz), 1.50–1.75 (1H, bs), 3.55 (1H, q, J=7.0Hz), 3.59 (2H, s), 3.75 (3H, s), 4.68 (1H, dd, J=2.6, 11.6Hz), 5.00 (1H, dd, J=2.9, 11.6Hz), 6.42–6.52 (1H, m), 6.70–6.90 (1H, m), 6.82 (2H, d, J=8.7Hz), 6.90–7.05 (2H, m), 7.05–7.35 (5H, m), 7.56–7.67 (1H, m)

REFERENCE EXAMPLE 7

In a mixed solvent of 100 ml of THF and 30 ml of water was dissolved 10.0 g (20.0 mmol) of 2-(2,4-difluorophenyl)-2-hydroxy-3-((4-methoxyphenyl)methylthio)-3-methylbutyl (S)-(+)-2-phenylpropionate ($[\alpha]^{25}$+15.9° (c=1.09, MeOH)), and 1.68 g (40.0 mmol) of lithium hydroxide monohydrate was added thereto in divided portions with stirring under ice-cooling. The mixture was warmed to room temperature and stirred for 30 hours. To the reaction mixture was added diethyl ether, and the mixture was extracted with ethyl acetate. The organic layer was washed successively with a saturated sodium hydrogencarbonate aqueous solution and a saturated sodium chloride aqueous solution and dried. The solvent was removed by distillation under reduced pressure, and the residue was subjected to column chromatography using a mixed solvent of hexane and ethyl acetate (5:1) as an eluent. The solvent was removed by distillation under reduced pressure to obtain 7.3 g (99%) of (+)-2-(2,4-difluorophenyl)-3-((4-methoxyphenyl)methylthio)-3-methylbutane-1,2-diol as a colorless oily substance.

$[\alpha]^{25}$+32.1° (c=1.02, MeOH)
IR (film) $v_{max}$ cm$^{-1}$: 3484
NMR (CDCl$_3$) The data were identical with those obtained in Reference Example 5.

REFERENCE EXAMPLE 8

In 580 ml of pyridine was dissolved 70.0 g (0.19 mol) of (+)-2-(2,4-difluorophenyl)-3-((4-methoxy-phenyl)-methylthio)-3-methylbutane-1,2-diol, and 25.2 g (0.22 mol) of methanesulfonyl chloride was added dropwise thereto with stirring under ice-cooling. After being stirred for 3 hours, a solution of 32.0 g (0.57 mol) of potassium hydroxide in a mixed solvent of 340 ml of methanol and 340 ml of water was added dropwise to the mixture. After being warmed to room temperature, the mixture was stirred for 12 hours. The mixture was then acidified by slow addition of 850 ml of 4N hydrochloric acid with stirring under ice-cooling, followed by extraction with diethyl ether. The organic layer was washed successively with IN hydrochloric acid, a saturated sodium hydrogencarbonate aqueous solution, and a saturated sodium chloride aqueous solution, and dried. The solvent was removed by distillation under reduced pressure, and the residue was purified by column chromatography using a mixed solvent of hexane and ethyl acetate (100:1). The solvent was removed by distillation under reduced pressure, and the residue was recrystallized from a mixed solvent of hexane and diethyl ether to obtain 64.0 g (96%) of (−)-2-(2,4-difluorophenyl)-2-(1-((4-methoxyphenyl)methylthio)-1-methylethyl)oxirane as a colorless crystal.

Melting Point: 55–56° C.

$[\alpha]^{25}$ −20.2° (c = 1.00, MeOH)

IR (nujol) $\nu_{max}$ cm$^{-1}$: 966

NMR (CDCl$_3$): The data were identical with those obtained in Reference Example 4.

REFERENCE EXAMPLE 9

A mixture of 64.0 g (182 mmol) of (−)-2-(2,4-difluorophenyl)-2-(1-((4-methoxyphenyl)methylthio)-1-methylethyl)oxirane, 25.1 g (364 mmol) of 1,2,4-triazole, 50.3 g (364 mmol) of potassium carbonate, and 910 ml of DMF was stirred at 105° C. for 17 hours. After allowing the mixture to cool, the solvent was removed by distillation under reduced pressure, and to the residue were added dichloromethane and water. The organic layer was separated, washed with a saturated sodium chloride aqueous solution, and dried. The solvent was removed by distillation under reduced pressure, and the residue was purified by column chromatography using a mixed solvent of chloroform and methanol (30:1) as an eluent. The solvent was removed by distillation under reduced pressure to obtain 72.0 g (94%) of (+)-2-(2,4-difluorophenyl)-3-((4-methoxyphenyl)methylthio)-3-methyl-1-(1H-1,2,4-triazol-1-yl)butan-2-ol as a pale yellow oily substance.

$[\alpha]^{25}$ +8.4° (c = 1.21, MeOH)

IR (film) $\nu_{max}$ cm$^{-1}$: 3428

NMR (CDCl$_3$): 1.38 (3H, d, J = 3.2Hz), 1.40 (3H, s), 3.79 (3H, s), 3.89 (1H, d, J = 11.6Hz), 4.05 (1H, d, J = 11.9Hz), 5.00 (1H, d, J = 14.9Hz), 5.20–5.40 (1H, bs), 5.32 (1H, dd, J = 2.4, 13.9Hz), 6.59–6.70 (1H, m), 6.77–6.90 (1H, m), 6.84 (2H, d, J = 8.7Hz), 7.26 (2H, d, J = 8.6Hz), 7.65–7.80 (1H, m), 7.79 (1H, s), 8.25 (1H, s)

REFERENCE EXAMPLE 10

To 72.0 g (172 mmol) of (+)-2-(2,4-difluoro-phenyl)-3-((4-methoxyphenyl)methylthio)-3-methyl-1-(1H-1,2,4-triazol-1-yl)butan-2-ol were added 18.6 g (172 mmol) of anisole and 1010 ml of trifluoroacetic acid in this order, followed by stirring at 70° C. for 1.5 hours. After allowing the mixture to cool, the solvent was removed by distillation under reduced pressure, and the residue was neutralized with a saturated sodium hydrogencarbonate aqueous solution, followed by extraction with dichloromethane. The organic layer was washed with a saturated sodium chloride aqueous solution and dried. The solvent was removed by distillation under reduced pressure, and the residue was purified by column chromatography using chloroform as an eluent. The solvent was removed by distillation under reduced pressure, and the residue was recrystallized from a mixed solvent of isopropyl ether and hexane to obtain 44.1 g (86%) of (−)-2-(2,4-difluoro-phenyl)-3-mercapto-3-methyl-1-(1H-1,2,4-triazol-1-yl)butan-2-ol as a colorless crystal.

Melting Point: 105° C.

$[\alpha]^{25}$ −49.8° (c = 1.08, MeOH)

IR (nujol) $\nu_{max}$ cm$^{-1}$: 3412

NMR (CDCl$_3$): 1.38 (3H, s), 1.44 (3H, d, J = 2.3Hz), 2.38 (1H, s), 4.96 (1H, dd, J = 2.0, 14.0Hz), 5.25–5.55 (1H, bs), 5.34 (1H, dd, J = 2.2, 13.8Hz), 6.60–6.75 (1H, m), 6.75–6.90 (1H, m), 7.60–7.75 (1H, m), 7.78 (1H, s), 8.23 (1H, s)

REFERENCE EXAMPLE 11

In 5 ml of THF was dissolved 2.0 g (6.7 mmol) of (31)-2-(2,4-difluorophenyl)-3-mercapto-3-methyl-1-(1H-1,2,4-triazol-1-yl)butan-2-ol, and 1.4 g of a methanol solution containing 0.394 g (7.3 mmol) of sodium methoxide was added thereto dropwise with stirring under ice-cooling. After being stirred for 5 minutes, the solution was added dropwise to a solution of 3.0 g (20 mmol) of 3,6-dichloropyridazine in 5 ml of THF while stirring under ice-cooling. The reaction mixture was warmed to room temperature and stirred for 12 hours, followed by distillation under reduced pressure to remove the solvent. To the residue were added dichloromethane and a saturated sodium chloride aqueous solution. The organic layer was separated, washed with a saturated sodium chloride aqueous solution, and dried. The solvent was removed by distillation under reduced pressure, and the residue was purified by column chromatography using a mixed solvent of chloroform and methanol (100:1) as an eluent. The solvent was removed by distillation under reduced pressure to obtain 1.4 g (51%) of (+)-3-(6-chloropyridazin-3-ylthio)-2-(2,4-difluorophenyl)-3-methyl-1-(1H-1,2,4-triazol-1-yl)butan-2-ol as an oily substance.

$[\alpha]^{25}$ +90.3° (c = 0.98, MeOH)

IR (film) $\nu_{max}$ cm$^{-1}$: 3416, 1618

NMR (CDCl$_3$): 1.56 (3H, s), 1.61 (3H, d, J = 3.1Hz), 4.84 (1H, dd, J = 1.8, 14.0Hz), 5.40 (1H, d, J = 13.9Hz), 6.65–6.85 (2H, m), 7.43 (1H, d, J = 9.0Hz), 7.51 (1H, d, J = 9.0Hz), 7.65–7.80 (1H, m), 7.78 (1H, s), 7.85–8.05 (1H, bs), 8.37 (1H, s)

REFERENCE EXAMPLE 12

In the same manner as in Reference Examples 7 to 11 and Example 1, (−)-2-(2,4-difluorophenyl)-3-methyl-1-(1H-1,2,4-triazol-1-yl)-3-(6-(1H-1,2,4-triazol-1-yl)-pyridazin-3-ylthio)butan-2-ol was obtained from 2-(2,4-difluorophenyl)-2-hydroxy-3-((4-methoxyphenyl)methylthio)-3-methylbutyl (S)-(+)-2-phenylpropionate ($[\alpha]^{25}$ +13.3° (c = 1.03, MeOH)).

Melting Point: 221–224° C.

$[\alpha]^{25}$ −133.9° (c = 1.05, CHCl$_3$)

IR (nujol) $\nu_{max}$ cm$^{-1}$: The data were identical with those obtained in Example 1.

NMR (CDCl$_3$): The data were identical with those obtained in Example 1.

FORMULATION EXAMPLE 1

| Compound of Example 1 | 50 mg |
| --- | --- |
| Lactose | 200 mg |
| Crystalline cellulose | 40 mg |
| Magnesium stearate | 5 mg |

The above components were mixed and punched out in a known manner to obtain tablets each containing 50 mg of the active ingredient.

FORMULATION EXAMPLE 2

| Compound of Example 1 | 50 mg |
| --- | --- |
| Lactose | 90 mg |
| Corn starch | 60 mg |
| Talc | 30 mg |
| Magnesium stearate | 10 mg |

The above components were mixed and granulated in a known manner to obtain granules.

FORMULATION EXAMPLE 3

| Compound of Example 1 | 2.0 g |
| --- | --- |
| White vaseline | 25.0 g |
| Stearyl alcohol | 25.0 g |
| Propylene alcohol | 12.0 g |
| Sodium lauryl sulfate | 1.5 g |
| Ethyl p-hydroxybenzoate | 0.5 g |
| Distilled water | 34.0 ml |

The above components were uniformly mixed in a known manner to obtain a cream.

FORMULATION EXAMPLE 4

To 2.5 g (1.7 mmol) of maltosyl-$\beta$-cyclodextrin was added 2 ml of distilled water for injectable solutions to dissolve it, and 86.6 mg (0.18 mmol) of a hydrochloride of (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol (compound of Example 1) was added thereto, followed by stirring to prepare a clear paste. The paste was dissolved in 10 ml of distilled water for injectable solutions and adjusted to pH 6 with 1N sodium hydroxide. Distilled water for injectable solutions was further added thereto to give a total volume of 20 ml. The solution was filtered through Ekicrodisc (produced by German Science Japan; pore size: 0.2 $\mu$m) to prepare a 4 mg/ml solution. The solution was filled in an ampule and sterilized to obtain an injection.

FORMULATION EXAMPLE 5

To 25 g (17 mmol) of maltosyl-$\beta$-cyclodextrin was added 20 ml of distilled water for injectable solutions to dissolve it, and 866 mg (1.8 mmol) of a hydrochloride of (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol (compound of Example 1) was added thereto, followed by stirring to prepare a clear paste. The paste was dissolved in 200 ml of distilled water for injectable solutions, followed by filtration through Ekicrodisc (produced by German Science Japan; pore size: 0.2 $\mu$m). The filtrate was lyophilized to obtain 25 g of a white inclusion complex.

| Inclusion complex | 1000 mg |
| --- | --- |
| Crystalline cellulose | 100 mg |
| Corn starch | 70 mg |
| Talc | 20 mg |
| Magnesium stearate | 10 mg |

The above components were mixed and granulated in a known manner to prepare granules containing 30 mg of the compound of Example 1 per 1.2 g.

FORMULATION EXAMPLE 6

To 1.38 g (1.2 mmol) of $\beta$-cyclodextrin was added 2 ml of distilled water for injectable solutions, 0.18 g (0.37 mmol) of a hydrochloride of (+)-2-(2,4-difluorophenyl)3-methyl-1-(1H-1,2,4-triazol-1-yl)-3-(6-(1H-1,2,4-triazol-1-yl)pyridazin-3-ylthio)butan-2-ol (compound of Example 1) was added thereto, followed by stirring to prepare a clear paste. To the paste was added 100 ml of distilled water for injectable solutions, followed by filtration through Ekicrodisc (produced by German Science Japan; pore size: 0.2 $\mu$m). The filtrate was lyophilized to obtain 1.5 g of a white inclusion complex.

| Inclusion complex | 1000 mg |
| --- | --- |
| Crystalline cellulose | 100 mg |
| Corn starch | 70 mg |
| Talc | 20 mg |
| Magnesium stearate | 10 mg |

The above components were mixed and granulated in a known manner to prepare granules containing 100 mg of the compound of Example 1 per 1.2 g.

TEST EXAMPLE 1

Plasma Level

Two beagles per group each received an oral preparation of an inclusion complex composed of the compound of Example 1 and maltosyl-$\beta$-cyclodextrin ($G_2$-$\beta$-CyD) at a dose of 10 mg of the compound of Example 1 per kg-b.w. or an intravenous injection of the inclusion complex at a dose of 5 mg of the compound of Example 1 per kg-b.w. For comparison, a suspension of the compound of Example 1 in 0.5% methyl cellulose (MC) was orally administered at a dose of 10 mg per kg-b.w. A-blood sample was taken at 0.5, 1, 2, 3, 5, 8, and 24 hours after administration. After deproteination, the concentration of the compound of formula (I) in the sample was determined by high performance liquid chromatography (HPLC). The results obtained are shown in Table 1 and FIG. 1.

TABLE 1

Plasma Concentrations of Compound 1 in Dogs

| Dosage Form | Route | Dose (mg/kg) | Plasma Concentration ($\mu$g/ml) | | | | | | |
| --- | --- | --- | --- | --- | --- | --- | --- | --- | --- |
| | | | 0.5 h | 1 h | 2 h | 3 h | 5 h | 8 h | 24 h |
| $G_2$-$\beta$-Cyd | i.v. | 5 | 4.1 | 3.4 | 2.8 | 2.0 | 1.7 | 1.3 | 0.3 |
| $G_2$-$\beta$-Cyd | p.o. | 10 | 2.5 | 2.8 | 2.9 | 2.6 | 2.5 | 2.2 | 0.7 |
| MC | p.o. | 10 | 0.3 | 0.3 | 0.3 | 0.2 | 0.4 | 0.3 | 0.2 |

In the FIG. 1, the plasma concentration is plotted as the ordinate and the time after administration as the abscissa. The hollow square indicates the $G_2$-$\beta$-CyD (i.v.) group; the solid circle the $G_2$-$\beta$-Cyd (p.o.) group; and the solid square the MC (p.o.) group. As is apparent from FIG. 1, the compound of the present invention exhibits markedly increased absorption from the gastrointestinal tract when used as an inclusion complex with a cyclodextrin derivative.

TEST EXAMPLE 2

In Vitro Antifunqal Activity

*Candida albicans* ($10^2$ cells) or *Aspergillus fumigatus* ($10^3$ cells) was inoculated to 200 $\mu$l of an Eagle's minimum essential medium containing 10% fetal bovine serum and a test compound shown in Table 2 below at a dilution increasing by a factor of 2. The system was incubated at 37° C. for 24 hours in a 5 v/v% $CO_2$ stream to obtain the minimum inhibitory concentration (MIC) on mycelium formation. The results obtained are shown in Table 2.

TABLE 2

| Test Compound | MIC on Mycelium Formation ($\mu$g/ml) | |
| --- | --- | --- |
| | *C. albicans* | *A. fumicatus* |
| Example 1 | 0.05 | 3.13 |
| Reference | 1.56 | 100 |

TABLE 2-continued

| | MIC on Mycelium Formation (μg/ml) | |
|---|---|---|
| Test Compound | C. albicans | A. fumicatus |
| Example 12 | | |

The results in Table 2 prove that the dextrorotatory enantiomer of the present invention (compound of Example 1) is superior to the corresponding levorotatory enantiomer (Reference Example 12) in antifungal activity.

TEST EXAMPLE 3

In Vivo Antifuncal Activity

*Asperoillus fumigatus* Kawasaki strain having been cultured at 27° C. for 1 week was suspended in physiological saline, and the suspension (3×10⁶ cells) was injected into the tail vein of a 4-week-old day male mouse (9 mice per group). Two days before the infection and on the day of the infection, 100 mg/kg of cyclophosphamide was intraperitoneally administered to each animal. From 1 hour after infection, 25 mg/kg of a test compound suspended in 0.5% MC or in the form of an inclusion complex with maltosyl-β-cyclodextrin was orally given to each animal twice a day for 4 consecutive days, and the life or death of the animals was observed for 10 days.

For comparison, compound (A) shown below which is described in EP 0421210A2, fluconazole (FCZ) and itraconazole (ITZ), were used as a comparative substance. Itraconazole was administered in a polyethylene glycol (400) solution.

Compound (A)

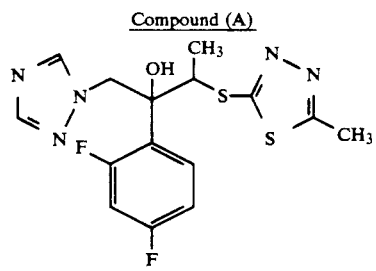

The results obtained are shown in Table 3.

TABLE 3

| | Survival Number on Day | | | | | | | | | | Mean Survival |
|---|---|---|---|---|---|---|---|---|---|---|---|
| Compounds | 1 | 2 | 3 | 4 | 5 | 6 | 7 | 8 | 9 | 10 | Days |
| Example 1 (MC) | 9 | 9 | 9 | 5 | 5 | 4 | 4 | 2 | 2 | 2 | 5.9 |
| Example 1 (G₂-β-CyD) | 9 | 9 | 9 | 9 | 9 | 9 | 9 | 9 | 9 | 9 | >10 |
| A(MC) | 9 | 9 | 3 | 0 | | | | | | | 2.3 |
| FCZ(MC) | 9 | 9 | 0 | | | | | | | | 2.0 |
| ITZ(PEG) | 9 | 9 | 9 | 1 | | | | | | | 2.1 |
| Control (MC) | 9 | 7 | 0 | | | | | | | | 1.8 |

It is seen from Table 3 that the compound of the present invention exhibits more potent antifungal activity against *Aspergillus fumigatus* in p.o. than either of compound (A), fluconazole, and itraconazole and is thus proved to be an excellent antifungal drug.

TEST EXAMPLE 4

In Vivo Antifungal Activity

*Candida albicans* CAA-14 strain having been cultured at 30° C. for 24 hours was suspended in physiological saline, and the cell suspension (5×10⁶ cells) was injected into the tail vein of a 5-week-old ICR male mouse (9 mice per group). Two days before the infection and on the day of the infection, 100 mg/kg of cyclophosphamide was intraperitoneally administered to each animal. From 1 hour after the infection, an aqueous solution of 5 mg/kg of a test compound in the form of an inclusion complex with maltosyl-β-cyclodextrin was injected into the tail vein of each animal twice a day for two consecutive days, and the life or death of the animals was observed for 10 days.

For comparison, fluconazole was used as a comparative substance.

The results obtained are shown in Table 4.

TABLE 4

| | Survival Number on Day | | | | | | | | | | Mean Survival |
|---|---|---|---|---|---|---|---|---|---|---|---|
| Compounds | 1 | 2 | 3 | 4 | 5 | 6 | 7 | 8 | 9 | 10 | Days |
| Example 1 (G₂-β-CyD) | 9 | 9 | 9 | 9 | 9 | 9 | 9 | 9 | 9 | 9 | >10.0 |
| FCZ (Saline) | 9 | 9 | 8 | 8 | 8 | 6 | 3 | 2 | 2 | 1 | 6.3 |
| Control (Saline) | 3 | 0 | | | | | | | | | 0.3 |

It is seen from Table 4 that the compound of the present invention exhibits more potent antifungal activity against *Candida albicans* in i.v. than fluconazole, and is thus proved to be an excellent antifungal drug.

TEST EXAMPLE 5

In Vivo Antifungal Activity

*Aspergillus fumigatus* Kawasaki strain having been cultured at 27° C. for 1 week was suspended in physiological saline, and the cell suspension (3×10⁶ cells) was injected into the tail vein of a 4-week-old day male mouse (9 mice per group). Two days before the infection and on the day of the infection, 100 mg/kg of cyclophosphamide was intraperitoneally administered to each animal. From 1 hour after the infection, an aqueous solution of 12.5 mg/kg of a test compound in the form of an inclusion complex with maltosyl-β-cyclodextrin was injected into the tail vein of each animal twice a day for 4 consecutive days, and the life or death of the animals was observed for 10 days.

For comparison, fluconazole was used as a comparative substance.

The results obtained are shown in Table 5.

TABLE 5

| | Survival Number on Day | | | | | | | | | | Mean Survival |
|---|---|---|---|---|---|---|---|---|---|---|---|
| Compounds | 1 | 2 | 3 | 4 | 5 | 6 | 7 | 8 | 9 | 10 | Days |
| Example 1 (G₂-β-CyD) | 9 | 9 | 9 | 9 | 8 | 8 | 8 | 7 | 7 | 7 | >9.0 |
| FCZ (Saline) | 9 | 9 | 0 | | | | | | | | 2.0 |
| Control (Saline) | 9 | 9 | 0 | | | | | | | | 2.0 |

It is seen from Table 5 that the compound of the present invention exhibits more potent antifungal activity against *Aspergillus fumigatus* in i.v. than fluconazole and is thus proved to be an excellent antifungal drug.

TEST EXAMPLE 6

Acute Toxicity

A 5-week-old ICR male mouse (5 mice per group) having been deprived of solid food and liquids for 24 hours was orally given 1000 mg/kg of the compound of Example 1 or the compound (A) suspended in 0.5% MC, and the life or death thereof was observed for 7 days. No case of death was observed in the group of the compound of Example 1, while in the group of the compound (A) all of the mice died. From these results, the compound of the present invention proved to have an obviously lower toxicity than the compound (A).

TEST EXAMPLE 7

Toxicity in Maintained Administration

A 6-week-old Crj:CD male rat (6 rats per group) was maintained on the compound of Example 1 or fluconazole suspended in 0.5% MC at a dose of 100 mg/kg or 300 mg/kg once a day for 2 consecutive weeks. Manifestations of toxicity were observed through observation of general signs, body weight measurement, biochemical examination of blood, organ weight measurements, and postmortem examinations.

No case of death was observed in any group. The fluconazole group revealed production of hepatomegaly and enlargement of the suprarenalcapsules, with the degree thereof depending on dosage. The group of the compound of the present invention showed no noticeable damage, except for slight hepatic hypertrophy. With respect to the degree of hepatomegaly, the pathologic findings in the group maintained on 300 mg/kg of the compound of the present invention were almost the same as those in the group maintained on 100 mg/kg of fluconazole. From all these results, the compound of the present invention proved to have an obviously lower toxicity than fluconazole.

As having been proved by the above-described test examples, the compound according to the present invention has an excellent effect as an antifungal drug.

While the invention has been described in detail and with reference to specific examples thereof, it will be apparent to one skilled in the art that various changes and modifications can be made therein without departing from the spirit and scope thereof.

What is claimed is:

1. (+)-2-(2,4-Difluorophenyl)-3-methyl-1-(1H-1,2,4-triazol-1-yl)-3-(6-(1H-1,2,4-triazol-1-yl)pyridazin-3-ylthio)butan-2-ol represented by formula (I):

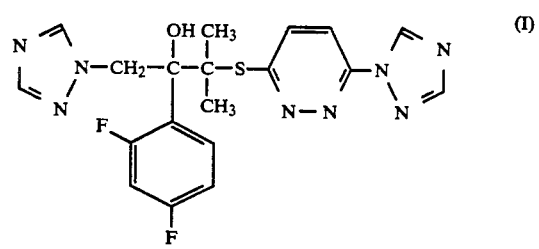

or a pharmaceutically acceptable salt thereof.

2. An antifungal composition containing (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol represented by formula (I):

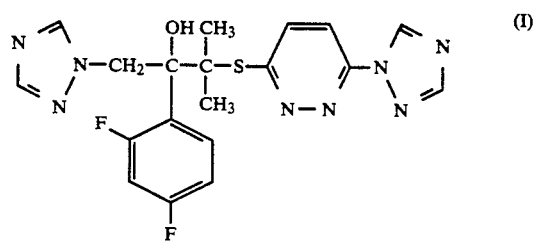

or a pharmaceutically acceptable salt thereof as an active ingredient.

3. An antifungal composition mainly comprising an inclusion complex composed of (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol represented by formula (I):

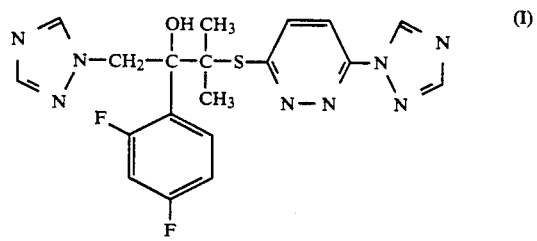

or a pharmaceutically acceptable salt thereof and cyclodextrin.

4. The antifungal composition of claim 3, wherein the cyclodextrin is a β-cyclodextrin.

5. The antifungal composition of claim 3, wherein the cyclodextrin is a hydroxyethyl cyclodextrin.

6. The antifungal composition of claim 3, wherein the cyclodextrin is a glucosyl cyclodextrin.

7. The antifungal composition of claim 3, wherein the cyclodextrin is a maltosyl cyclodextrin.

8. The antifungal composition of claim 7, wherein the maltosyl cyclodextrin is maltosyl-β-cyclodextrin.

9. A method for treating a human suffering from candidosis, aspergillosis or cryptococcosis, comprising, administering to said human the composition of claim 2 in a therapeutic amount.

10. A method for treating a human suffering from candidosis, aspergillosis or cryptococcosis, comprising, administering to said human the composition of claim 3 in a therapeutic amount.

* * * * *